United States Patent [19]

Hara

[11] Patent Number: 4,802,101
[45] Date of Patent: Jan. 31, 1989

[54] SIGNAL PROCESSING METHOD FOR DETERMINING BASE SEQUENCE OF NUCLEIC ACID

[75] Inventor: Makoto Hara, Kaisei, Japan
[73] Assignee: Fuji Photo Film Co., Ltd., Japan
[21] Appl. No.: 897,999
[22] Filed: Aug. 19, 1986
[30] Foreign Application Priority Data Aug. 19, 1985 [JP] Japan ................... 60-181432

[51] Int. Cl.4 ............................................. G01N 33/58
[52] U.S. Cl. ................................. 364/496; 364/413.01; 435/6; 935/77
[58] Field of Search ............... 364/487, 496, 497, 498, 364/413; 250/303, 327.2, 484.1; 204/299 R, 301, 182.8; 435/6; 935/77

[56] References Cited

U.S. PATENT DOCUMENTS

| | | | |
|---|---|---|---|
| 4,524,420 | 6/1985 | Glodo et al. | 364/497 |
| 4,617,468 | 10/1986 | Shiraishi et al. | 250/484.1 |
| 4,624,769 | 11/1986 | Simada et al. | 204/299 R |
| 4,665,312 | 5/1987 | Shiraishi et al. | 250/303 |
| 4,720,786 | 1/1988 | Hara | 364/413 |

*Primary Examiner*—Parshotam S. Lall
*Assistant Examiner*—V. N. Trans
*Attorney, Agent, or Firm*—Gerald J. Ferguson, Jr.

[57] ABSTRACT

A signal processing method for determining base sequence of nucleic acids by subjecting digital signals to signal processing, said digital signals corresponding to an autoradiograph of a resolved pattern which is formed by resolving a mixture of base-specific DNA fragments or base-specific RNA fragments labeled with a radioactive element in one-dimensional direction on a support medium, which comprises steps of:

(1) preparing at least two one-dimensional waveforms for each band, with position along the resolving direction as abscissa and signal level as ordinate;
(2) detecting positions at which signal level is maximum on each waveform; and
(3) comparing the positions having maximum signal level detected on the plural waveforms for each band to determine a position of said band.

8 Claims, 2 Drawing Sheets

SIGNAL PROCESSING METHOD FOR DETERMINING BASE SEQUENCE OF NUCLEIC ACID

BACKGROUND OF THE INVENTION

1. Field of the Invention

This invention relates to a signal processing method for determining base sequence of nucleic acids.

2. Description of the Prior Art

It is essential to obtain genetic information carried by organisms in order to make the function or replication mechanism of the organism clear in the field of molecular biology which has been rapidly developed in recent years. Particularly, it is essential to determine base sequence of nucleic acids such as DNA (or DNA fragment; the same applies hereinbelow) which carries specific genetic information.

Maxam-Gilbert method and Sanger-Coulson method are known as typical methods for determining the base sequence of nucleic acids such as DNA and RNA. In the former Maxam-Gilbert method, a group containing a radioactive isotope such as $^{32}P$ is attached to a chain molecule of DNA or a DNA fragment at one end to label it with the radioactive element and then the bond between the constitutional units of the chain molecule is base-specifically cleaved by a chemical reaction. A mixture of the resulting base-specific DNA cleavage products is resolved (developed) through gel electrophoresis to obtain a resolved pattern (not visible) wherein each of the numerous cleavage products is resolved on the gel support medium. The resolved pattern is visualized on a radiographic film such as an X-ray film to obtain an autoradiograph thereof as a visible image. The bases in certain positional relationships with the end of the radioactive element-attached chain molecule can be sequentially determined according to the visualized autoradiograph and the applied base-specific cleavage means. In this way, the sequence for all bases of the DNA specimen can be determined.

In the latter Sanger-Coulson method, synthetic DNA products which are complementary to the chain molecule of DNA or DNA fragment and radioactively labeled, are base-specifically synthesized by utilizing a chemical reaction, and the obtained mixture of numerous synthetic DNA products is resolved on a support medium by gel electrophoresis to obtain a resolved pattern. In a similar manner to that described above, the base sequence of DNA can be determined according to the visualized autoradiograph.

For the purpose of carrying out the determination of the base sequence of nucleic acids simply with high accuracy in autoradiography, there are described in U.S. patent applications Ser. No. 837,037 and No. 664,405 autoradiographic procedures which utilize a radiation image recording and reproducing method using a stimulable phosphor sheet, in place of the above-mensioned conventional radiography using a radiosensitive material such as an X-ray film. The stimulable phosphor sheet comprises a stimulable phosphor and has such properties that when exposed to a radiation, the stimulable phosphor absorbs a portion of radiation energy and then emits light (stimulated emission) corresponding to the radiation energy stored therein upon excitation with an electromagnetic wave (stimulating rays) such as visible light or infrared rays. According to this method, exposure time can be greatly shortened and there is no fear of causing problems such as chemical fog associated with prior arts. Further, since the autoradiograph having information on radioactively labeled substances is stored in the phosphor sheet as radiation energy and then read out as stimulated emission in time sequence, information can be expressed by the form of numerals and/or symbols in addition to image.

The base sequence of the nucleic acids has been conventionally determined by visually judging individual resolved positions of the base-specific cleavage products or the base-specific synthetic products of radioactively labeled nucleic acid (hereinafter referred as to simply base-specific fragments of nucleic acid) on the autoradiograph and comparing them among the resolved rows thereof. Namely, the analysis of the autoradiograph is done by observing the visualized autoradiograph with eyes, and such visual analysis requires great amounts of time and labor.

Further, since the visual analysis of the autoradiograph varies or fluctuates owing to the skill of investigators, the results on the determination of the base sequence of nucleic acid vary depending on the investigators and the accuracy of information is limited to a certain extent.

In order to improve the accuracy of the information, there are proposed in U.S. patent applications Ser. No. 568,877 and No. 730,034 methods for automatically determining the base sequence of DNA by obtaining the autoradiograph as digital signals and subjecting the digital signals to appropriate signal processing. The digital signals corresponding to the autoradiograph can be obtained either by visualizing the autoradiograph on a radiographic film and photoelectrically reading out the visible image on said film by means of reflected light or transmitted light when the conventional radiography is employed, or by directly reading out the stimulable phosphor sheet without the visualization of the autoradiograph when the radiation image recording and reproducing method is employed.

However, the resolved pattern obtained by resolving (developing) radioactively labeled substances on a support medium by electrophoresis or the like is liable to cause various distortion and noise. For example, bands (resolved portions), which are in the shape of rectangle extending perpendicularly to the resolving direction, tend to be not strictly perpendicular (horizontal) thereto but inclined due to unevenness of a support medium per se such as production of damages or holes on the surface thereof, fluctuation of gel concentration, or contamination thereof with impurities; or deformation of the shapes of slots (sample introducing ports). Once the inclination of a band occurs during the resolution, bands resolved and separated after said band are also apt to be observed with the inclination similar thereto. In such case, the resolved positions of the bands are difficult to be accurately determined and the distorted bands causes an error in the determination of the sequence of bands over the resolved rows based on the band positions.

Accordingly, it is highly demanded to automatically determine the base sequence of nucleic acids with high accuracy by subjecting digital signals corresponding to the autoradiograph to efficient signal processing, even when such band distortion is caused.

SUMMARY OF THE INVENTION

The present inventor has found that the base sequence of the nucleic acids can be automatically determined with easiness and high accuracy by suitably processing the digital signals corresponding to the autoradiograph in the method for the automatic determination of the base sequence using autoradiography, even when the resolved pattern causes the band distortion.

The present invention provides a signal processing method for determining base sequence of nucleic acids by subjecting digital signals to signal processing, said digital signals corresponding to an autoradiograph of a resolved pattern which is formed by resolving a mixture of base-specific DNA fragments or base-specific RNA fragments labeled with a radioactive element in one-dimensional direction on a support medium, which comprises steps of:

(1) preparing at least two one-dimensional waveforms for each band, with position along the resolving direction as abscissa and signal level as ordinate;

(2) detecting positions at which signal level is maximum on each waveform; and (3) comparing the positions having maximum signal level detected on the plural waveforms for each band to determine a position of said band.

According to the present invention, the base sequence of a nucleic acid can be simply determined with high accuracy by processing digital signals corresponding to the autoradiograph of the resolved pattern which is formed on a support medium by resolving a mixture of base-specific fragments of the nucleic acid, through a suitable signal processing circuit having a function capable of making correction for the distortion of bands, when the resolved pattern causes the band distortion.

More in detail, digital signals are detected in such a manner that plural signals are obtained in the longitudinal direction (direction of the width) of a band and then subjected to the suitable signal processing such as a comparison operation processing, whereby the positions of bands can be accurately determined even when the individual bands are not perpendicular to the resolving direction but inclined. On the basis of the determined band positions, the bands are compared and collated over the resolved rows to determine the base sequence of the nucleic acid easily and with high accuracy.

DETAILED DESCRIPTION OF THE INVENTION

Figure 1:
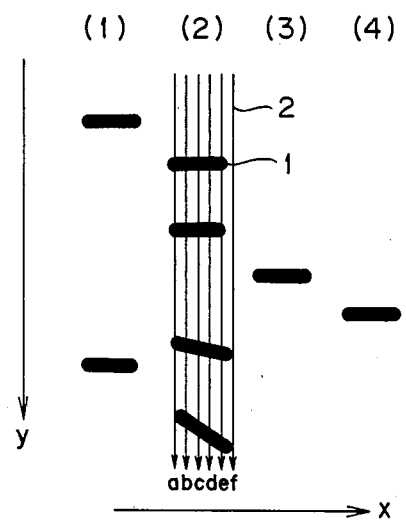
FIG. 1 is a partial view showing an example of an electrophoretic pattern which locally causes inclination of bands.

Examples of samples employable in the present invention include mixtures of base-specific fragments of nucleic acids such as DNA and RNA labeled with a radioactive element. The term "fragments" of nucleic acids mean portions of a long-chain molecule. For instance, a mixture of base-specific DNA cleavage products, which is a kind of a mixture of base-specific DNA fragments, can be obtained by base-specifically cleaving the radioactively labeled DNA according to the aforementioned MaxamGilbert method. A mixture of base-specific DNA synthetic products can be obtained by synthesizing from radioactively labeled deoxynucleoside triphosphates and DNA polymerase by use of DNA as a template according to the aforementioned Sanger-Coulson method.

Mixtures of base-specific RNA fragments can be also obtained as a mixture of cleavage products or a mixture of synthetic products in the similar manner to the DNA methods. DNA is composed of four kinds of bases: adenine, guanine, thymine and cytosine as its constitutional units, and RNA is composed of four kinds of bases: adenine, guanine, uracil and cytosine. These substances can be labeled with a radioactive element such as $^{32}P$, $^{14}C$, $^{35}S$, $^3H$ or $^{125}I$ by any of appropriate methods.

A sample, which is a mixture of the base-specific fragments of a nucleic acid labeled with a radioactive element, can be resolved (developed) on a known support medium such as a gel support medium by any of conventional resolving (developing) procedures such as electrophoresis, thin layer chromatography, column chromatography and paper chromatography.

The support medium on which the radioactively labeled substances are resolved, is autoradiographed by means of the conventional radiography using a radiosensitive material or the radiation image recording and reproducing method using a stimulable phosphor sheet. The digital signals corresponding to the autoradiograph are then obtained through an appropriate read-out system.

When the conventional radiography is used, the support medium and a radiosensitive material such as an X-ray film are placed together in layers at a low temperature of −90 to −70° C. for a long period of time (several tens of hours) to expose the radiographic film. The radiographic film is then developed to visualize the autoradiograph of the radioactively labeled substances on the film, and the visualized autoradiograph is read out by using an image read-out system. For instance, the radiographic film is irradiated with an optical beam and the beam transmitted thereby or reflected therefrom is photoelectrically detected, whereby the visualized autoradiograph can be transformed to electric signals. Further, the electric signals are converted into digital signals corresponding to the autoradiograph through A/D conversion.

When the radiation image recording and reproducing method is used, the support medium and the stimulable phosphor sheet are placed together in layers at an ambient temperature for a short period of time (several seconds to several tens of minutes) to store radiation energy radiating from the radioactively labeled substances in the phosphor sheet, whereby the autoradiograph is recorded as a kind of a latent image (energy-stored image) on the prosphor sheet. The stimulable phosphor sheet, for instance, has a basic structure where a support comprising a plastic film, a phosphor layer comprising a stimulable phosphor such as a divalent europium activated barium fluorobromide phosphor ($BaFBr:Eu^{2+}$) and a transparent protective film are laminated in this order. The stimulable phosphor has characteristics of absorbing and storing radiation energy when irradiated with a radiation such as X-rays and subsequently releasing the stored radiation energy as stimulated emission when excited with visible light to infrared rays.

Then, the autoradiograph stored and recorded on the stimulable phosphor sheet is read out by using a read-out system. For instance, the phosphor sheet is scanned with a laser beam to release the radiation energy stored in the stimulable phosphor as light emission and the emitted light is photoelectrically detected, so that the autoradiograph can be directly obtained as electric signals without the visualization thereof. Further, the electric signals are converted into digital signals corresponding to the autoradiograph through A/D conversion.

The above-described methods for measuring the autoradiograph and obtaining the digital signals corresponding thereto are described in more detail in the aforementioned U.S. patent applications Ser. No. 837,037 and No. 568,877.

While the methods for obtaining the digital signals corresponding to the autoradiograph using the conventional radiography and the radiation image recording and reproducing method are described above, the present invention is not limited thereto and digital signals obtained by any other methods can be applied to the signal processing method of the invention, provided that they correspond to the autoradiograph.

In the above read-out procedures, it is not always necessary to conduct the read-out operation of the autoradiograph all over the surface of the radiographic film or the stimulable phosphor sheet. Only the image region may be subjected to the read-out operation.

In the present invention, there may be previously inputted information on the location of each resolved row and the width of band to preset read-out conditions and then conducted scanning at a scanning line density such that each band is traversed by at least two scanning lines in the read-out operation, so as to shorten read-out time and obtain efficiently necessary information. The digital signals corresponding to the autoradiograph in the invention also include the thus-obtained digital signals.

The obtained digital signals $D_{xy}$ comprise a coordinate (x,y) which is represented by a coordinate system fixed to the radiographic film or the stimulable phosphor sheet and a signal level (z) at the coordinate. The signal level represents the density of image at the coordinate, that is, the amount of the radioactively labeled substances. Accordingly, a series of the digital signals (namely, digital image data) have information on two-dimensional location of the labeled substances.

The digital signals corresponding to the autoradiograph of the radioactively labeled substances resolved on a support medium, is subjected to signal processing to determine the base sequence of nucleic acid according to the invention described in more detail below.

Now, the signal processing method of the present invention will be described by referring to an example of an electrophoretic pattern formed with a combination of the following four groups of base-specific DNA fragments labeled with a radioactive element:

(1) guanine (G) - specific DNA fragments,
(2) adenine (A) - specific DNA fragments,
(3) thymine (T) - specific DNA fragments,
(4) cytosine (C) - specific DNA fragments.

Each group of said base-specific DNA fragments is composed of base-specific cleavage products or synthetic products which have various lengths and the same base at terminals.

FIG. 1 partially shows an autoradiograph of the electrophoretic pattern obtained by electrophoresing the above four groups of the base-specific DNA fragments in four slots, respectively.

The digital signals corresponding to the autoradiograph are stored temporarily in a memory device of the signal processing circuit (that is, stored in a non-volatile memory unit such as a buffer memory, a magnetic disk, etc.).

In the first place, at least two one-dimensional waveforms are prepared for each band on each electrophoretic row (lane). The one-dimensional waveform is a graph with position in the electrophoretic direction as abscissa and signal level as ordinate. When the detection of the digital signals are carried out by scanning with the laser beam along each lane at such a scanning line density that at least two scanning lines traverse each band as described above (see: FIG. 1; 1: electrophoretic band, 2: scanning line and FIG. 4, step 10), the one-dimensional waveform with signal level (z) as vertical axis and position (y) as horizontal axis can be directly prepared for every scanning line.

Figure 2:
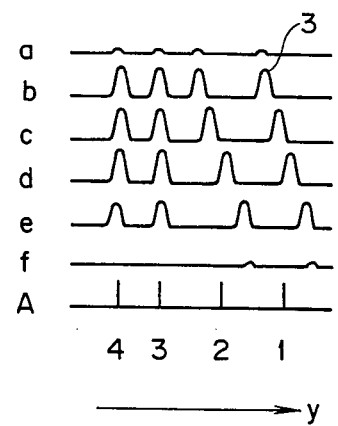
FIG. 2 shows one-dimensional waveforms for the second slot.

FIG. 2 partially shows one-dimensional waveforms a to f for the second slot. The waveforms represent a cross-sectional image obtained when bands are cut off along the electrophoretic direction.

Figure 4:
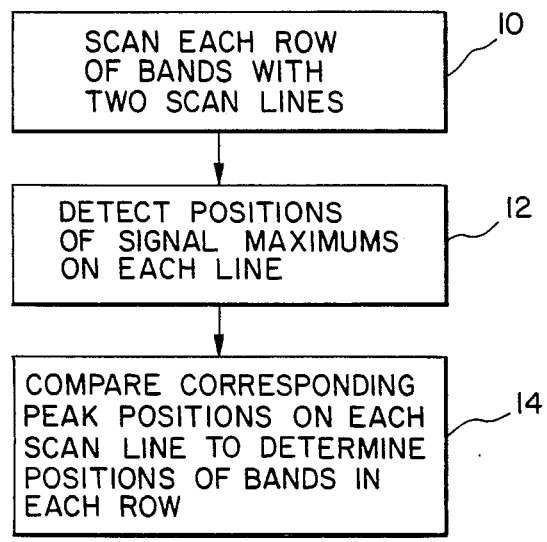
FIG. 4 is a flow chart of an illustrative program implementing the invention.

In the second place, positions (peak positions) where the signal level is maximum are detected, see step 12 of FIG. 4. For example, the peak positions are detected by finding out points where the sign of a difference in signal level is inverted (see: FIG. 2; 3: peak position).

In the third place, the peak positions detected on the plural one-dimensional waveforms for each band are compared to decide a position of the band, see step 14 of FIG. 4. For example, the detected peak positions are consecutively numbered for each waveform and thereby the peak positions having the same number and neighboring on each other can be taken as belonging to the same band. More in detail, the waveform (e.g., waveforms c and d in FIG. 2) having high signal levels and one or two more waveforms on each side thereof are considered, and an average position, a maximum position or a minimum position of the peak positions having the same number on these waveforms is calculated.

In FIG. 2, A indicates positions of the bands finally decided by taking an average of the peak positions on the waveforms b to e for each band.

From the viewpoint of the accuracy, it is usually preferred to take the average of peak positions as the band position. When the fine holes produced in the gel support medium or the impurities incorporated therein locally prevent the sample from electrophoresing regularly, the maximum of peak positions (the position in the largest migration distance therebetween) is preferably taken as the band position. Alternatively, when the slot is inclined to the electrophoretic direction, the minimum of peak positions (the position in the smallest migration distance therebetween) may be taken as the band position.

Thus, the band positions can be individually determined even when the bands are inclined.

When the electrophoretic pattern causes various distortion and noise such as a smiling phenomenon, offset distortion and combining of bands, the digital signals may be subjected to signal processing for correction therefor before or after the above-described processing for the correction for the band distortion.

The smiling phenomenon is a phenomenon in which migration distances of the radioactively labeled substances at the both sides of the support medium are shorter than that in the vicinity of the center thereof. The smiling phenomenon is caused by heat dissipation effect (so-called edge effect), etc. during the electrophoresis. The offset distortion is a phenomenon in which positions of the lanes are wholly deviated from one another and is caused by difference between the slots in the electrophoresis-starting position or time of samples, which is due to the unevenness of the shapes of slots, etc. The combining of bands is a phenomenon in which two or three bands are combined together to form one broad band and is caused by the insufficient electrophoresis. Usually, the combined bands tend to be appeared in the upper region of the pattern near the electrophoresisstarting position.

The signal processing methods for the correction for the smiling phenomenon, the offset distortion and the combining of bands are described in our co-pending Japanese Patent Applications No. 60(1985)-74899, No. 60(1985) -75900, No. 60(1985)-85275, No. 60(1985)-85276, No. 60(1985)-111186 and No. 60(1985)-111187 (the whole content of which corresponds to U.S. patent applications Ser. No. 849,187, No. 854,381 and No. ).

All the bands are sequenced directly by comparing the decided band positions with each other. The sequence can be easily determined on the basis of the fact that two or more bands can not be detected at the same positions of the lanes since a combination of the above four groups of the base-specific DNA fragments is exclusive from each other. The four slots (1) to (4) have information on the terminal base of (G), (A), (T) and (C), respectively, so that the substitution of the band sequence with bases corresponding to the slots which the individual bands belong to gives the base sequence of DNA. For instance, the base sequence of DNA can be obtained as:

A - G - C - T - A - A - G ......

In these ways, the base sequence of one chain molecule of DNA can be determined. The representation mode of the information on the base sequence of DNA is by no means limited to the above-mentioned mode, and other representation modes may be employed optionally. For instance, the intensity (z') of each band can be together denoted as the relative amount of the radioactively labeled substances, if desired. The base sequence of both two chain molecules of DNA can be also represented.

The information can be also displayed as an image on the basis of the above processed digital signals. At the same time, the original autoradiograph can be displayed as a visualized image. In this case, investigators themselves can finally determine the DNA sequence on the basis of the display image.

In the above-mentioned example, there is described the case where the exclusive combination of the mixture (G, A, T, C) of base-specific DNA fragments as a sample is used, but the signal processing method of the present invention is by no means limited to this combination, and other combinations can be used. For instance, a combination of (G, G+A, T+C, C) can be used. Further, the signal processing method of the invention can be also applied to the mixtures (for instance, a combination of G, A, U, C) of base-specific RNA fragments. Moreover, the correction for the band distortion is not limited to one set of resolved rows of base-specific fragments of a nucleic acid, but can be made on all resolved rows simultaneously resolved on a support medium.

It is possible to perform the genetic philological information processing such as collation between the obtained base sequence of the DNA and the base sequence of another DNA which has been already recorded and stored in a suitable means.

Figure 3:
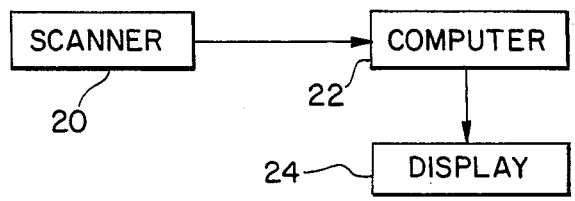
FIG. 3 is an illustrative block diagram of a system which may be employed to practice the invention.

The information on the base sequence of DNA determined through the above-described signal processing is output from the signal processing circuit, and subsequently transmitted to a recording device directly or optionally via storage in a storage means such as a magnetic disk or a magnetic tape. Referring to FIG. 3, there is illustrated an overall system which may be employed to practice the invention including a scanner 20, a computer 22, and a display 24.

Various recording devices based on various systems can be employed for recording the information, for example, a device for visualizing optically by scanning a photosensitive material with a laser beam, etc., a display means for visualizing electrically on CRT, etc., a means for printing symbols and/or numerals displayed on CRT by means of a video printer, and a means for visualizing on a heatsensitive recording material using thermic rays.

I claim:

1. A signal processing method for determining base sequence of nucleic acids by subjecting digital signals to signal processing, said digital signals corresponding to an autoradiograph of a resolved pattern which is formed by resolving a mixture of base-specific DNA fragments or base-specific RNA fragments labeled with a radioactive element in one-dimensional direction on a support medium, bands of the fragments desirably extending perpendicular to the one-dimensional direction of a row of said bands, which comprises steps of:
    (1) preparing at least two one-dimensional waveforms for each band where each waveform is substantially parallel in direction to said row, with position along the resolving direction as abscissa and signal level as ordinate;
    (2) detecting positions at which signal level is maximum on each waveform;
    (3) comparing the positions having maximum signal level detected on the plural waveforms for each band to determine a position of said band ; and
    (4) utilizing said position of said band to determine said base sequence of said nucleic acids.

2. The signal processing method as claimed in claim 1, wherein said digital signals are obtained by scanning the autoradiograph in such a manner that each band is traversed by at least two scanning lines, and in said step (1), the one-dimensional waveforms are prepared for the individual scanning lines.

3. The signal processing method as claimed in claim 1, wherein said position of the band is determined as an average of the positions having maximum signal level detected on the plural waveforms, in said step (3).

4. The signal processing method as claimed in claim 1, wherein said position of the band is determined as the greatest one of the positions having maximum signal level detected on the plural waveforms, in said step (3).

5. The signal processing method as claimed in claim 1, wherein said position of the band is determined as the least one of the positions having maximum signal level detected on the plural waveforms, in said step (3).

6. The signal processing method as claimed in claim 1, wherein the mixture of the base-specific DNA fragments consists of the four groups of:
  (1) guanine-specific DNA fragments;
  (2) adenine-specific DNA fragments;
  (3) thymine-specific DNA fragments; and
  (4) cytosine-specific DNA fragments;
and the resolved pattern consists of four rows formed by resolving each of said four groups of the base-specific DNA fragments on the support medium.

7. The signal processing method as claimed in claim 1, wherein said digital signals corresponding to the autoradiograph are obtained by placing the support medium and a stimulable phosphor sheet comprising a stimulable phosphor together in layers to record the autoradiograph of the resolved pattern on the phosphor sheet as an energy-stored image, irradiating said phosphor sheet with stimulating rays and photoelectrically detecting the autoradiograph as stimulated emission.

8. The signal processing method as claimed in claim 1, wherein said digital signals corresponding to the autoradiograph are obtained by placing the support medium and a radiosensitive material together in layers to record the autoradiograph of the resolved pattern on the radiosensitive material as a visible image and photoelectrically reading out the autoradiograph visualized on said radiosensitive material.

* * * * *